United States Patent
Tanaka et al.

(10) Patent No.: US 6,632,448 B2
(45) Date of Patent: Oct. 14, 2003

(54) PROCESS FOR PRODUCING L-ARABINOSE, L-ARABINOSE-CONTAINING ENZYMATICALLY PROCESSED PRODUCTS, DIET FOODS, DIABETIC DIET FOODS AND FRUIT OR VEGETABLE JUICES AND PROCESS FOR PRODUCING THE SAME

(75) Inventors: Hiromi Tanaka, Kyoto (JP); Genichi Yoshikawa, Kyoto (JP); Katsuyuki Mukai, Kyoto (JP); Yosihiro Nisikawa, Kyoto (JP); Akemi Morimoto, Kyoto (JP)

(73) Assignee: Unitika Ltd., Hyogo (JP)

( * ) Notice: Subject to any disclaimer, the term of this patent is extended or adjusted under 35 U.S.C. 154(b) by 0 days.

(21) Appl. No.: 09/937,775

(22) PCT Filed: Jan. 31, 2001

(86) PCT No.: PCT/JP01/00667
§ 371 (c)(1),
(2), (4) Date: Oct. 1, 2001

(87) PCT Pub. No.: WO01/57230
PCT Pub. Date: Aug. 9, 2001

(65) Prior Publication Data
US 2003/0040489 A1 Feb. 27, 2003

(30) Foreign Application Priority Data

| Nov. 2, 1999 | (JP) | 2000-336099 |
| Feb. 1, 2000 | (JP) | 2000-024121 |
| Jul. 25, 2000 | (JP) | 2000-224013 |
| Sep. 22, 2000 | (JP) | 2000-288745 |
| Nov. 2, 2000 | (JP) | 2000-336097 |

(51) Int. Cl.$^7$ .............................................. A61K 47/00
(52) U.S. Cl. ................. 424/439; 424/400; 424/94.1; 514/866
(58) Field of Search ................. 424/400, 439, 424/94.1; 514/866

(56) References Cited

U.S. PATENT DOCUMENTS 5,958,474 A * 9/1999 Lee et al. ..................... 426/50

* cited by examiner

Primary Examiner—Thurman K. Page
Assistant Examiner—Charesse Evans
(74) Attorney, Agent, or Firm—Sughrue Mion, PLLC

(57) ABSTRACT

Processes for conveniently and economically producing L-arabinose, enzyme-treated products containing L-arabinose, diet foods and diabetic foods containing L-arabinose with dietary fiber, and fruit or vegetable juices containing L-arabinose are provided.

(1) A process for producing L-arabinose by treating a natural material containing arabinan, arabinoxylan or arabinogalactan with an enzyme having an activity of acting on natural substances containing arabinan, arabinoxylan or arabinogalactan and thus releasing L-arabinose to give L-arabinose, characterized in that the above-described natural substance is directly treated with the above-described enzyme without separating or extracting arabinan, arabinoxylan or arabinogalactan.

(2) A process for producing a diet food and a diabetic food characterized by comprising treating a dietary fiber material originating in a natural substance containing arabinan, arabinoxylan or arabinogalactan with an enzyme which degrades arabinan, arabinoxylan or arabinogalactan to give an enzyme-treated product containing L-arabinose and dietary fiber, and adding the thus obtained enzyme-treated product to a food.

(3) An L-arabinose-containing fruit or vegetable juice characterized by containing an L-arabinose-containing fraction obtained by treating a fruit or vegetable press cake containing arabinan, arabinoxylan or arabinogalactan with an enzyme, and a process for producing the same.

26 Claims, 2 Drawing Sheets

PROCESS FOR PRODUCING L-ARABINOSE, L-ARABINOSE-CONTAINING ENZYMATICALLY PROCESSED PRODUCTS, DIET FOODS, DIABETIC DIET FOODS AND FRUIT OR VEGETABLE JUICES AND PROCESS FOR PRODUCING THE SAME

TECHNICAL FIELD

This invention relates to a process for producing L-arabinose, enzyme-treated products containing L-arabinose and a process for producing the same, and diet foods, diabetic foods and fruit or vegetable juices with the use of the same, and processes for the production thereof.

BACKGROUND ART

L-Arabinose is a non-caloric sweetener which has taste characteristics similar to sucrose and shows little absorbability. It is also known that L-arabinose inhibits enzymes which hydrolyze dissacharides such as sucrose and thus exerts an effect of suppressing an increase in blood glucose level due to the intake of sucrose. Using these characteristics of L-arabinose, there have been known body fat accumulation inhibitors (JP-A-7-309765, JP-A-7-242551), preventives and remedies for diseases related tohyperglycemia (JP-A-6-65080), diet sweeteners and preventives for obesity (JP-X-6-812057) and pet foods (JP-A-2-299555) each containing L-arabinose (the term "JP-A" as used herein means an "unexamined published Japanese patent application" and "JP-X" as used herein means a publication of Japanese translation of a PCT patent application). Also, L-arabinose is a saccharide which is useful as a starting material for synthesizing drugs.

L-Arabinose occurs as arabinan, arabinoxylan, arabinogalactan and the like in hemicellulose of higher plants. Also, a trace amount of L-arabinose in a free state is contained in fermented foods such as miso and sake, instant coffee, etc. Thus, L-arabinose is a saccharide which has been commonly taken over a long time.

It has been a practice to produce L-arabinose by alkali-extracting hemicellulose contained in corn fiber, gum arabic, beet pulp, etc., followed by acidolysis (JP-A-11-313700, JP-A-11-113600).

However, these acidolysis methods cannot be regarded as satisfactory, since these methods suffer from some problems such that carcinogens unsuitable for food and drug materials are likely formed, a special reaction apparatus should be employed in the acid treatment performed at 100° C. or higher, and a large amount of a salt is formed in the step of neutralization and thus a troublesome post-treatment is needed. Moreover, a troublesome procedure and a high cost are needed in the alkali-extraction of various hemicelluloses from natural substances. Further, there arises an additional problem such as the disposal method and spot of the waste remaining after the acquisition of L-arabinose while taking the effects thereof on the environment into consideration.

It is proposed to produce L-arabinose by treating beet pulp employed as the starting material with an alkali under heating followed by precipitation with ethanol, then acidolyzing or treating with an enzyme the thus extracted arabinan (JP-A-9-299093; J. Soc. of Agr. Chem., vol. 49 (6), pp.295–305, 1975). However, this method suffers from a problem that a troublesome procedure is required in the extraction of arabinan from the starting natural substance. Therefore, this method has been considered as little applicable to the industrial and economical production of L-arabinose because of the extremely low yield of L-arabinose established thereby.

In the report of Spagnuolo et al. (Biotechnology and Bioengineering, vol. 64(6), pp.685–691, 1999), L-arabinose could be obtained at a high yield. However, this method is unsuitable for the mass production of L-arabinose, since a deproteinization treatment of treating beet pulp with a protease and filtering, and an autoclaving treatment (121° C., 20 minutes) are needed as pretreatments in this method, which makes the procedure complicated.

On the other hand, conventional diet foods involve products containing konnyaku, etc. which give a feeling of fullness and yet have low caloric values, products containing low caloric sweeteners as a substitute for sugar, and products containing drugs having anorexic or sweetness-repellent effects.

However, there is no sweetener superior in taste characteristics to sugar. Use of less digestive components which merely give a feeling of fullness (konnyaku, etc.) or addition of drugs having the above-described effects, etc. cannot be considered as a favorable means of providing pleasant eating habits.

Many of conventional diabetic foods for regulating total calorie intake are unappetizing. Although calorie intake can be easily controlled in the hospital, preparation of calorie-restricted foods, injection of insulin for inhibiting an increase in blood glucose level and intake of drugs impose serious burden and stress both in mind and body of patients after discharge from the hospital.

Conventional juices, which are obtained by pressing fruits, etc., contain little L-arabinose as a monosaccharide. On the other hand, press juice cakes obtained in the production of juices are rich in L-arabinose in the form of polysaccharides. Although only a portion thereof is utilized as feeds and the like, they are mostly dumped as waste. That is to say, L-arabinose remaining therein is not effectively utilized at the present stage.

Although some of the conventional juices contain ground fruits, etc. or small pieces thereof, these juices merely containing ground fruits, etc. or small pieces thereof contain only an extremely small amount of L-arabinose as a monosaccharide. The polysaccharides such as arabinan, arabinoxylan or arabinogalactan, which are contained in a large amount in the ground fruits, etc. or small pieces thereof, are not degraded into L-arabinose in the human large intestine but mostly excreted. Therefore, it is considered that these products contain almost no additional component other than fiber from a nutritional viewpoint, though they are improved in the eating quality, i.e., feeling in the mouth, touch to the tongue, etc.

Although L-arabinose has valuable functions, the conventional processes for producing L-arabinose cost a great deal as described above and thus the practical utilization of L-arabinose as a starting material for foods, drugs, etc. is disturbed thereby. An object of the invention is to provide a process for economically producing L-arabinose and enzyme-treated products containing L-arabinose obtained from natural substances containing arabinan, arabinoxylan or arabinogalactan and a process for producing the same.

Although L-arabinose is sufficiently usable as a low caloric component to be employed in diet foods or diabetic foods, its content in foods should have been restricted due to the high cost caused by the troublesome handling procedures in the conventional processes for producing it. As a result, it is difficult to fully utilize the functions of L-arabinose.

Although dietary fiber inherently has sufficient functions, it has been employed hitherto almost exclusively for ameliorating intestinal disorders. Thus, it is not sufficiently expected as exerting the diet effect. In case of using as a material for diabetic foods, moreover, it is feared that dietary fiber would fail to achieve the effect of controlling the blood glucose level.

Another object of the invention is to provide diet foods or diabetic foods which have enhanced functions of L-arabinose to thereby make it possible to reduce the content of L-arabinose in foods and also posses the functions of dietary fiber, and a process for economically and conveniently producing the same.

Another object of the invention is to provide fruit or vegetable juices containing L-arabinose having functions such as an effect of inhibiting an increase in the blood glucose level, which is considered to be achieved by the effect of L-arabinose of inhibiting disaccharide-hydrolyzing enzymes, imparted thereto by adding an L-arabinose-containing press juice cake or a solution obtained by solid/liquid separation thereof to conventional juices.

DISCLOSURE OF THE INVENTION

In order to achieve these objects, the inventors have conducted extensive studies. As a result, they have found out that L-arabinose can be economically produced by treating a natural material containing arabinan, arabinoxylan or arabinogalactan directly with an enzyme having an activity of acting on natural substances containing arabinan, arabinoxylan or arabinogalactan and thus releasing L-arabinose without separating or extracting arabinan, arabinoxylan or arabinogalactan from the natural substance containing arabinan, arabinoxylan or arabinogalactan.

They have further found out that the effect of inhibiting an increase in blood glucose level after meal can be enhanced by adding dietary fiber together with L-arabinose to foods. They have furthermore found out that dietary fiber can be obtained together with L-arabinose by treating a dietary fiber material originating in a natural substance containing arabinan, arabinoxylan or arabinogalactan with a specific enzyme.

Moreover, they have found out that juices containing L-arabinose can be produced by treating press juice cake directly with an enzyme having an activity of acting on natural substances containing arabinan, arabinoxylan or arabinogalactan and thus releasing L-arabinose to give L-arabinose-containing press juice cake and then adding it, either as such or as an L-arabinose-containing fraction obtained after pressing, to juices.

The invention has been thus completed. Namely, the gist of the first embodiment of the invention resides in a process for producing L-arabinose by treating a natural material containing arabinan, arabinoxylan or arabinogalactan with an enzyme having an activity of acting on natural substances containing arabinan, arabinoxylan or arabinogalactan and thus releasing L-arabinose to give L-arabinose, characterized in that the above-described natural substance is directly treated with the above-described enzyme without separating or extracting arabinan, arabinoxylan or arabinogalactan. The gist of the second embodiment of the invention resides in an enzyme-treated product containing L-arabinose characterized in that a natural substance containing arabinan, arabinoxylan or arabinogalactan contains L-arabinose. The gist of the third embodiment of the invention resides in a process for producing an enzyme-treated product containing L-arabinose characterized by comprising releasing L-arabinose by treating a natural substance containing arabinan, arabinoxylan or arabinogalactan directly with an enzyme having an activity of acting on natural substances containing arabinan, arabinoxylan or arabinogalactan and thus releasing L-arabinose to give the enzyme-treated product containing L-arabinose as described above.

The gist of the fourth embodiment of the invention resides in a diet food characterized by containing L-arabinose and dietary fiber wherein it is preferable that the L-arabinose and dietary fiber employed are obtained by treating a dietary fiber material originating in a natural substance containing arabinan, arabinoxylan or arabinogalactan with an enzyme. The gist of the fifth embodiment of the invention resides in a process for producing a diet food characterized by comprising treating a dietary fiber material originating in a natural substance containing arabinan, arabinoxylan or arabinogalactan with an enzyme which degrades arabinan, arabinoxylan or arabinogalactan to give an enzyme-treated product containing L-arabinose and dietary fiber and adding the thus obtained enzyme-treated product to a food.

The gist of the sixth embodiment of the invention resides in a diabetic food characterized by containing L-arabinose and dietary fiber wherein it is preferable that the L-arabinose and dietary fiber employed are obtained by treating a dietary fiber material originating in a natural substance containing arabinan, arabinoxylan or arabinogalactan with an enzyme. The gist of the seventh embodiment of the invention resides in a process for producing a diabetic food characterized by comprising treating a dietary fiber material originating in a natural substance containing arabinan, arabinoxylan or arabinogalactan with an enzyme which degrades arabinan, arabinoxylan or arabinogalactan to give an enzyme-treated product containing L-arabinose and dietary fiber and adding the thus obtained enzyme-treated product to a food.

The gist of the eighth embodiment of the invention resides in an L-arabinose-containing fruit or vegetable juice characterized by containing an L-arabinose-containing fraction obtained by treating a fruit or vegetable press cake containing arabinan, arabinoxylan or arabinogalactan with an enzyme. The gist of the ninth embodiment of the invention resides in a process for producing an arabinose-containing fruit or vegetable juice characterized by comprising treating a fruit or a vegetable containing arabinan, arabinoxylan or arabinogalactan to divide into a juice and a press juice cake, treating the press juice cake with an enzyme to release L-arabinose and then adding the fraction containing the released L-arabinose to the juice.

BEST MODE FOR CARRYING OUT THE INVENTION

Figure 1:
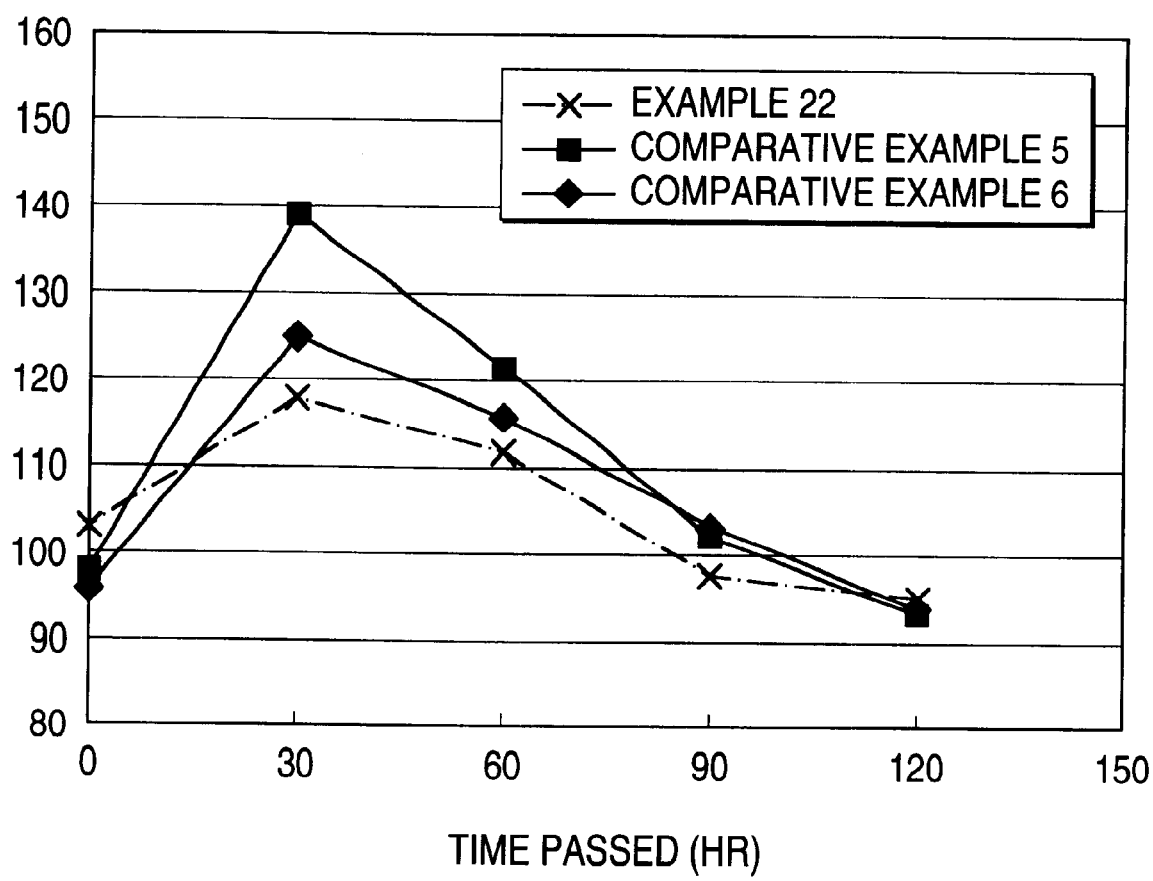
FIG. 1 is a graph which shows the data concerning the effect of inhibiting an increase in blood glucose level in Example 26.

First, the process for producing L-arabinose and an enzyme-treated product containing L-arabinose will be described in detail.

Examples of the material containing arabinan, arabinoxylan or arabinogalactan to be used in the invention include apple, beet, soybean, corn, rice, wheat and by-products obtained as residues in processing these materials such as orange fiber, mandarin orange juice cake, apple fiber, apple juice cake, beet fiber, beet pulp, peanut hull, rice bran, corn cake, soybean cake, corn fiber and peanut oil press cake. It is highly favorable to use wastes or by-products as the starting material not only because the production cost can be lowered thereby but also from the viewpoint of environmental protection by the effective utilization of industrial wastes. Orange fiber and mandarin orange juice cake, which are the residues remaining after pressing juice from orange, contain about 3 to 10% of L-arabinose in the form of arabinan, etc. Apple fiber, which is the residues remaining after pressing juice from apple, contains about 4 to 7% by weight of L-arabinose in the form of arabinan, etc. Beet pulp, which is the residue (press cake) remaining after pressing liquid sugar from beet (also called sugar beet) and optionally having been processed (adding molasses, drying, pelletizing, etc.), contains about 12 to 18% of L-arabinose in the form of arabinan, etc. Peanut cake, which consists of peanut hull, etc., contains about 5% of L-arabinose in the form of arabinan, etc. Arabinan contained in these materials is characterized by having a linear structure consisting of L-arabinose molecules attached to one another and L-arabinose can be relatively easily formed therefrom by an enzyme. From this point of view, beet pulp, apple fiber, orange fiber and the like, from which L-arabinose can be easily released, is considered as favorable materials. In addition, rice bran and corn fiber containing arabinoxylan and soybean cake containing arabinogalactan are usable as favorable materials.

Use can be made of natural substances containing arabinan, arabinoxylan or arabinogalactan with any origin or production process, so long as they are obtained by usual pressing methods.

Examples of the enzyme to be used in the invention, which has an activity of acting on natural substances containing arabinan, arabinoxylan or-arabinogalactan and thus releasing L-arabinose, include arabinan-decomposing enzymes such as arabinase (arabanase) and arabinofuranosidase. The origin of the arabinan-decomposing enzymes are exemplified by bacteria (*Bacillus subtilis*, Streptomyces sp.), yeasts (Rhodotorula sp.) and fungi (*Aspergillus niger, A. oryzae, A. pulverulentus, A. terreus, A. japonicus, A. flavus, Trichoderma reesei, T. viride, Trichosporon penicillatum*, Rhizopus sp.). Among all, enzymes originating in Aspergillus are appropriate and one originating in *Aspergillus niger* is particularly preferable.

These enzymes are produced in the culture supernatant or in the cells obtained by culturing the above-described strains by a known method. In the present invention, any fractions containing these enzymes may be used. If needed, fractions containing these enzymes may be purified or partially purified by conventional methods and used. It is also possible to use marketed enzymes. It is particularly preferable in the invention to use an arabinase Sumizyme ARS (manufactured by Shin Nihon Kagaku Kogyo K.K.) as a marketed enzyme with a high activity.

Moreover, marketed cellulase and hemicellulase preparations (xylanase, pectinase, galactanase, etc.) sometimes exhibit an activity of releasing L-arabinose upon acting on substances containing arabinan, arabinoxylan or arabinogalactan. This is because these enzymes sometimes have the activity of decomposing arabinan, arabinoxylan or arabinogalactan in addition to the indicated activity, or contain enzymes decomposing arabinan, arabinoxylan or arabinogalactan as contaminants in addition to the enzymes serving as the main component. In the invention, use can be also made of these enzymes having an activity of acting on materials containing arabinan, arabinoxylan or arabinogalactan and thus releasing L-arabinose, though they are usually employed as enzymes other than the enzymes decomposing arabinan, arabinoxylan or arabinogalactan. Among all, pectinase is favorable. Examples of the origins of pectinases include bacteria (*Bacillus subtilis*, Streptomyces sp., Erwinia sp.), Yeasts (*Saccharomyces cerevisiae*), fungi (*Aspergillus niger, A. alliaceus, A. fkavus, A. pulverulentus, A. japonicus, Trichosporon penicillatum*, Rhizopus sp., *Trichoderma ressei*), higher plants and the like. Enzymes originating in Aspergillus are most desirable. These pectinases are produced in the culture supernatant or cells obtained by culturing the above-described strains by a known method. In the invention, any fractions containing these enzymes may be used. If needed, fractions containing these enzymes may be purified or partially purified by conventional methods and used. It is also possible to use marketed enzymes. Examples of the marketed enzymes include Sumizyme PX (manufactured by Shin Nihon Kagaku Kogyo K.K.), Sumizyme AP-2 (manufactured by Shin Nihon Kagaku Kogyo K.K.), Sumizyme SPC (manufactured by Shin Nihon Kagaku Kogyo K.K.), Sumizyme MC (manufactured by Shin Nihon Kagaku Kogyo K.K.), Pectinase PL "AMANO" (manufactured by Amano Seiyaku K.K.), Pectinase G "AMANO" (manufactured by Amano Seiyaku K.K.), Pectinase GL "AMANO" (manufactured by Amano Seiyaku K.K.), Cellulosin PC5 (manufactured by Hankyu Bioindustry CO., LTD.), Cellulosin PE60 (manufactured by Hankyu Bioindustry CO., LTD.), Cellulosin PEL (manufactured by Hankyu Bioindustry CO., LTD.), Cellulosin ME (manufactured by Hankyu Bioindustry CO., LTD.), Pectinase SS (manufactured by Yakult Pharmaceutical Ind. Co., Ltd.), Pectinase 3S (manufactured by Yakult Pharmaceutical Ind. Co., Ltd.), Pectinase HL (manufactured by Yakult Pharmaceutical Ind. Co., Ltd.), ROHAPECT D5L (manufactured by Higuchi Inc.), ROHAPECT D5S (manufactured by Higuchi Inc.), ROHAPECT MA PLUS (manufactured by Higuchi Inc.), ROHAPECT MAX (manufactured by Higuchi Inc.), ROHAPECT PTE (manufactured by Higuchi Inc.), ROHAPECT PL (manufactured by Higuchi Inc.), ROHAPECT BI (manufactured by Higuchi Inc.), ROHAPECT VR-C (manufactured by Higuchi Inc.), ROHAPECT 7104 (manufactured by Higuchi Inc.), ROHAPECT DA6L (manufactured by Higuchi Inc.), ROHAPECT 10L (manufactured by Higuchi Inc.), ROHAPECT AP1 (manufactured by Higuchi Inc.), Sucrase N (manufactured by Sankyo Co., Ltd.), Sucrase S (manufactured by Sankyo Co., Ltd.), Pectinex (manufactured by Novo Nordisk Bioindustry, Ltd.), Ultrazym (manufactured by Novo Nordisk Bioindustry, Ltd.), Vinozym (manufactured by Novo Nordisk Bioindustry, Ltd.), Citrozym (manufactured by Novo Nordisk Bioindustry, Ltd.), Olivex (manufactured by Novo Nordisk Bioindustry, Ltd.), Novopham 12 (manufactured by Novo Nordisk Bioindustry, Ltd.), Vinoflow (manufactured by Novo Nordisk Bioindustry, Ltd.), Peelzym (manufactured by Novo Nordisk Bioindustry, Ltd.) and Pectinase <NAGASE> (manufactured by Nagase Seikagaku Kogyo K.K.). In the invention, it is particularly preferable to use Sumizyme PX, which is a pectinase manufactured by Shin Nihon Kagaku Kogyo K.K., as a marketed enzyme with a high activity.

In the above case, the yield of L-arabinose can be elevated by mixing two or more of these enzymes having different activities. In particular, L-arabinose can be obtained at a high yield by the combined use of an enzyme which degrades arabinan, arabinoxylan or arabinogalactan with pectinase.

In addition to the enzymes as cited above, it is preferable to add a maceration enzyme capable of breaking plant cell wall to thereby elevate the yield of L-arabinose.

The amount of the enzyme having an activity of acting on materials containing arabinan, arabinoxylan or arabinogalactan and thus releasing L-arabinose is not particularly restricted. Namely, it may be used in such an amount as required in decomposing the arabinan, arabinoxylan or arabinogalactan in the starting material. In case of arabinase, for example, it is preferable to use 0.4 to 4000 U of the enzyme, preferably 2 to 2000 U and still preferably 4 to 1000 U, per 100 g of the starting material. The unit (U) as used herein is defined as the amount of enzyme whereby 1 $\mu$mol of L-arabinose is released from linear arabinan per minute.

In the process according to the invention, a material containing arabinan, arabinoxylan or arabinogalactan is treated with the enzyme. To treat directly, the material containing arabinan, arabinoxylan or arabinogalactan is suspended in an aqueous medium and then the enzyme is added thereto. Then the reaction is carried out under stirring or allowing to stand. The conditions of treating the material containing arabinan, arabinoxylan or arabinogalactan are not particularly restricted and conditions commonly employed in enzyme reactions may be employed therefor. Namely, the conditions may be appropriately determined depending on the optimum conditions of the enzyme employed and other factors.

It is preferable that the reaction temperature is controlled to a level at which the enzyme is not inactivated but microorganisms can hardly grow, thereby preventing putrefaction. More particularly speaking, the reaction temperature ranges from 20 to 90° C., preferably from 40 to 80° C. and still preferably from 50 to 75° C. Concerning the pH value of the liquid reaction mixture, it is needless to say that the reaction is carried out preferably under the optimum conditions of the enzyme. That is to say, the pH value is controlled preferably to 2 to 9, preferably 2.5 to 8 and still preferably 3 to 6. The reaction time depends on the amounts of the material containing arabinan, arabinoxylan or arabinogalactan and the enzyme. In general, it is preferable from the viewpoint of performance to set the reaction time to 3 to 48 hours As the reaction proceeds, the arabinan, arabinoxylan or arabinogalactan is hydrolyzed and L-arabinose thus formed is released. The obtained reaction mixture as it is, or after heating at 100° C. or above, or after further drying, is usable as the enzyme-treated product containing L-arabinose of the second embodiment of the invention. An L-arabinose sugar solution can be obtained by collecting the supernatant of the suspension after the completion of the reaction. The L-arabinose thus obtained may be purified by various chromatographic procedures commonly employed in the art with the use of ion exchange resins, active carbon, etc. Alternatively, crystalline L-arabinose may be obtained by adding hot ethanol to the solution containing L-arabinose thus obtained.

Next, the diet foods and the diabetic foods and processes for producing the same will be described in detail. As the starting materials of the diet foods and the diabetic foods, it is desirable to use the above-described materials containing arabinan, arabinoxylan or arabinogalactan and the enzymes as described above, though the invention is not restricted thereto. As the L-arabinose, use can be made of marketed products or those obtained by extracting hemicellulose contained in corn fiber, gum arabic, beet pulp, etc. with an alkali and then acidolyzing. Examples of the dietary fiber source include water-soluble dietary fibers such as polydextrose, sodium alginate and pectin and water-insoluble dietary fibers such as cellulose, lignin and hemicellulose. It is preferable to use dietary fiber obtained by treating dietary fiber materials originating in the above-described natural substances containing arabinan, arabinoxylan or arabinogalactan with enzymes.

The diet foods or diabetic foods according to the invention can be produced by treating a dietary fiber material originating in a natural material containing arabinan, arabinoxylan or arabinogalactan with an enzyme which degrades arabinan, arabinoxylan or arabinogalactan to give an enzyme-treated product containing L-arabinose and dietary fiber and adding the thus obtained enzyme-treated product to foods. Although the enzyme-treatment is carried out under the conditions as described above, it is also possible to form L-arabinose and dietary fiber at the same time under specific conditions to give the enzyme-treated product. Alternatively, conditions appropriate for the release of L-arabinose and conditions appropriate for the formation of dietary fiber may be successively employed to give the enzyme-treated product.

Next, the enzyme-treated product thus obtained is blended in the production process of foods. Examples of the foods usable herein include baked products such as wafers, crackers, biscuits, cookies and Western-style cakes, breads such as white bread, soft rolls, buns, croissants and stick breads, cereals, noodles, chocolates, candies, tablets, frozen products such as ice cream and sherbet, Japanese style cakes such as manju (bean-jam buns) and daifuku (soft rice cake with bean-jam) and ground fish paste products. In each case, it is preferable to add from 0.01 to 10% of L-arabinose and from 1 to 75% of dietary fiber based on the weight of the food.

Western-style cakes, breads, cereals, noodles, etc. are prepared usually by kneading cereal flour (wheat flour in most cases and rice flour in some cases), which is employed as the main component, together with saccharides such as sucrose, sodium chloride, water, butter, margarine, egg, etc. and then baking. Thus, the enzyme-treated product may be added in the step of blending the materials so as to give the above-described content based on the weight of the food.

Now, the $\alpha$-glucosidase inhibition mechanism of L-arabinose, which is the constituent feature of the invention, will be described in detail. According to the report of Susumu Hizukuri (J. Appl. Glucosic., Vol. 46, No. 2, pp. 159–165 (1999)), L-arabinose uncompetitively inhibits disaccharide-decomposing enzymes (maltase, sucrase, etc.) located on the surface of microchorions (mucociliary borders) in the duodenal and small intestinal mucosae. As a result, the incorporated carbohydrates are gradually degraded into glucose and fructose which are absorbed scarcely in the duodenum or the upper part of the jejunum but in the middle and lower parts of the small intestine. That is to say, monosaccharides are slowly absorbed in the whole small intestine. Thus, a rapid increase in blood glucose level (hyperglycemia) can be inhibited and an anorectic effect can be achieved by sustaining the feeling of fullness, thereby establishing a diet effect.

Moreover, the effect of inhibiting an increase in blood glucose level can be enhanced by simultaneously taking L-arabinose with dietary fiber, though the mechanism thereof is still unknown.

Next, the fruit and vegetable juices and the process for producing the same will be described in detail. As the materials for the fruit and vegetable juices, use can be made of those cited above concerning the process for producing L-arabinose. In addition, it is also possible to use citrus fruits, pear, strawberry, grape, peach, plum, radish, carrot, celery, tomato, sweet pepper, spinach, etc.

Such a material is divide into a juice and a press juice cake by treating in a conventional manner such as grinding and solid/liquid separation or pressing. From arabinan which is characterized in having a linear structure of L-arabinose, L-arabinose is relatively easily released by an enzyme-treatment. It is favorable to use apple juice press cake, orange juice press cake, etc. as the starting material, since about 90% or more of arabinan contained therein is released.

The enzyme to be used in treating the press juice cake containing arabinan, arabinoxylan or arabinogalactan, the amount of the enzyme and the reaction conditions may be determined as in the process of producing L-arabinose as described above.

As the reaction proceeds, polysaccharides such as arabinan, arabinoxylan or arabinogalactan in the juice press cake are hydrolyzed and L-arabinose is released. Thus, L-arabinose-containing juice press cake can be obtained. After the completion of the reaction, the cake is pressed to give an L-arabinose-containing solution. The thus obtained L-arabinose-containing press cake or the L-arabinose-containing fraction obtained by pressing is then added to a juice to give an L-arabinose-containing juice. The content of L-arabinose in the juice is controlled preferably to 0.001 to 10 g/L, still preferably 0.1 to 5 g/L.

Addition of the L-arabinose-containing fraction, which is obtained by treating a fruit or vegetable juice press cake with an enzyme, to juices makes it possible to produce juices having an enhanced effect of inhibiting an increase in blood glucose level compared with the case of adding L-arabinose alone.

To achieve effects as diet foods or diabetic foods or the effect of inhibiting an increase in blood glucose level, the daily intake of L-arabinose is controlled to 1 to 30 g, preferably 1.5 to 10 g.

EXAMPLES

Now, the invention will be described in greater detail by reference to the following examples.

In these examples, the saccharide concentrations of L-arabinose-containing materials were expressed in Brix % by way of convenience. Each Brix % was measured by using a HAND REFRACTO METER manufactured by ATAGO.

First, processes for producing L-arabinose will be illustrated.

Example 1

200 g of apple fiber (manufactured by Nichiro Corporation, moisture content: 2.3%) was suspended in 2 L of water. After adding 2 mL of Sumizyme ARS (arabinase manufactured by Shin Nihon Kagaku Kogyo K.K., titer: 400 U/mL), the mixture was reacted under stirring at 55° C. for 24 hours. After the completion of the reaction, the supernatant was filtered to give 1.9 L of a clear solution containing L-arabinose. Saccharides contained in this solution were analyzed by high-performance liquid column chromatography. The analysis was carried out by using an analytical column TSKgel Amide-80 (manufactured by Tosoh Corporation, 4.6 mm (i.d.)×25 cm) at a column temperature of 80° C. and a flow rate of 0.8 mL/min with the use of 80% acetonitrile as an eluent. Saccharides were detected by the fluorescence detection by using benzamidine derivatives and the L-arabinose content was determined based on the quantitative data of standards. As the result of the analysis of the solution obtained after the reaction as described above, 10 g of L-arabinose was accumulated in 1.9 L of the solution.

Next, this solution was passed successively through an anion exchange resin (Dowex SAR, OH$^-$ type, manufactured by The Dow Chemical Company, bed volume: 100 mL), a cation exchange resin (Dowex HCRW2, H$^+$ type, manufactured by The Dow Chemical Company, bed volume: 100 mL) and active carbon (Diahope S80 manufactured by Mitsubishi Chemical Corporation, bed volume: 100 mL) in this order and an L-arabinose-containing solution was thus collected. The collected solution was concentrated on an evaporator until its Brix attained 70 to give a sugar solution containing 8.6 g of L-arabinose.

Example 2

200 g of beet pulp (manufactured by Cargill, Inc., moisture content: 11%) was suspended in 2 L of water. After adding 2 mL of Sumizyme ARS (arabinase manufactured by Shin Nihon Kagaku Kogyo K.K., titer: 400 U/mL), the mixture was reacted under stirring at 55° C. for 24 hours. After the completion of the reaction, the mixture was allowed to stand and then the supernatant was filtered to give 1.9 L of a clear solution containing L-arabinose. Saccharides contained in this solution were analyzed in a similar manner as in Example 1. As a result, 27 g of L-arabinose was accumulated in 1.9 L of the solution.

Next, 10 g of powdery active carbon (Carborafin, manufactured by Takeda Chemical Industries, Ltd.) was added to the solution. After stirring for 20 minutes, a solution containing L-arabinose was collected by filtration. Then this solution was passed successively through an anion exchange resin (Diaion WA30, OH$^-$ type, manufactured by Mitsubishi Chemical Corporation, bed volume: 100 mL) and a cation exchange resin (Diaion SK1B, H$^+$ type, manufactured by Mitsubishi Chemical Corporation, bed volume: 100 mL) in this order and an L-arabinose-containing solution was thus collected. The collected solution was concentrated on an evaporator until its Brix attained 70. Then hot ethanol was added to give a final concentration of 85%. After adding a small amount of crystalline L-arabinose, the mixture was allowed to stand at 4° C. By filtering this solution, 25 g of crystalline L-arabinose was obtained. The melting point of the L-arabinose thus obtained was 157 to 160° C.

Next, a comparative example, wherein arabinan was once extracted and then an enzyme-treatment was carried out by reference to JP-A-9-299093, will be given.

Comparative Example 1

To 200 g of beet pulp (manufactured by Cargill, Inc., moisture content: 11%) was added 600 mL of a 2.5% calcium hydroxide solution. After immersing overnight, the mixture was heated to 100° C. for 12 hours, cooled and then adjusted to pH 6. After filtering, ethanol was added to the filtrate thus obtained to give a precipitate of arabinan. Then it was dissolved in water again, passed successively through an anion exchange resin (Diaion WA30, OH$^-$ type, manufactured by Mitsubishi Chemical Corporation, bed volume: 100 mL) and a cation exchange resin (Diaion SK1B, H$^+$ type, manufactured by Mitsubishi Chemical Corporation, bed volume: 100 mL) and dried to give 2.4 g of arabinan.

2.4 g of arabinan was suspended in 50 mL of water. After adding 0.025 mL of Sumizyme ARS (arabinase manufactured by Shin Nihon Kagaku Kogyo K.K., titer: 400 U/mL), the mixture was reacted under stirring at 55° C. for 24 hours.

After the completion of the reaction, the mixture was allowed to stand and then the supernatant was filtered to give 47 mL of a clear solution containing L-arabinose. Saccharides contained in this solution were analyzed in a similar manner as in Example 1. As a result, 1.3 g of L-arabinose was obtained in 47 mL of the solution.

By this process, 0.65% of L-arabinose was obtained based on the starting material. In contrast, 13.5% of L-arabinose was obtained based on the starting material in Example 2, showing a high yield. By the production process according to the invention, L-arabinose contained in beet pulp could be released and recovered at a yield higher than 70% (mass %) of L-arabinose contained therein. Namely, the problem of a decrease in the yield of L-arabinose caused by some treatments such as alkali-extraction has been solved by the invention.

Table 1 summarizes the L-arabinose yields achieved in Examples 1 and 2 and Comparative Example 1. Arabinan contents were determined in the following manner. 2 mL of 72% sulfuric acid was added to 20 mg of a starting material. After stirring for 1 hour, the reaction mixture was diluted 20-fold and maintained at 100° C. for 3 hours. The L-arabinose content thus released was quantified by the method described in Example 1 and the value thus obtained was referred to as the content of arabinan in the starting material.

Amount of the collected L-arabinose means the amount (g) of purified L-arabinose obtained form 200 g of the starting material. Yield means the ratio of the purified L-arabinose to the arabinan contained in the starting material.

TABLE 1

| | Starting material | Arabinan content (a) | Arabinose released from 200 g of starting material | Amount of collected arabinose (b) | Yield (c) |
|---|---|---|---|---|---|
| Ex. 1 | apple fiber | 5.2% | 10 g | 8.6 g | 82.7% |
| Ex. 2 | beet pulp | 17.0% | 27 g | 25.0 g | 73.5% |
| Comp. Ex. 1 | beet pulp | 17.0% | — | 1.3 g | 3.8% |

Note: (c) = (b) ÷ (200 × (a))

Example 3

To 200 g of beet pulp (manufactured by Toshoku, Ltd., moisture content: 11%) was added 2 L of an enzyme solution containing 1 mL of Sumizyme PX (pectinase manufactured by Shin Nihon Kagaku Kogyo K.K., pectinase titer: 6000 U/mL, arabinase titer 100 U/mL) dissolved therein. Then, the mixture was reacted under stirring at 55° C. for 24 hours. After the completion of the reaction, the supernatant was filtered to give 1.9 L of a clear solution containing L-arabinose. Saccharides contained in this solution were analyzed in a similar manner as in Example 1. As a result, 19 g of L-arabinose was accumulated in 1.9 L of the solution.

Next, this solution was passed successively through an anion exchange resin (Dowex SAR, OH⁻ type, manufactured by The Dow Chemical Company, bed volume: 100 mL), a cation exchange resin (Dowex HCRW2, H⁺ type, manufactured by The Dow Chemical Company, bed volume: 100 mL) and active carbon (Diahope S80 manufactured by Mitsubishi Chemical Corporation, bed volume: 100 mL) in this order and an L-arabinose-containing solution was thus collected. The collected solution was concentrated on an evaporator until its Brix attained 70 to give a sugar solution containing 17.5 g of L-arabinose.

Example 4

To 704 g of a press cake (moisture content: 74%) obtained after extracting soluble components containing sucrose as the main component from beet was added 1.5 L of an enzyme solution containing 4 mL of Sumizyme PX (pectinase manufactured by Shin Nihon Kagaku Kogyo K.K., pectinase titer: 6000 U/mL, arabinase titer 100 U/mL) dissolved therein. Then, the mixture was reacted under stirring at 55° C. for 24 hours. After the completion of the reaction, the supernatant was filtered to give 1.5 L of a clear solution containing L-arabinose. Saccharides contained in this solution were analyzed in a similar manner as in Example 1. As a result, 20 g of L-arabinose was accumulated in 1.5 L of the solution.

Next, processes for producing enzyme-treated products and enzyme-treated products containing L-arabinose and dietary fiber will be illustrated. In the following examples, L-arabinose was quantified by suspending 1 g of an enzyme-treated product in 100 mL of water, extracting the water-soluble fraction and then analyzing free saccharides contained in the enzyme-treated product as in Example 1.

Example 5

Enzyme-Treated Beet Pulp

To 200 g of beet pulp (manufactured by Cargill, Inc., moisture content: 11%) were added 600 mL of water and 2 mL of Sumizyme ARS (arabinase manufactured by Shin Nihon Kagaku Kogyo K.K., titer: 400 U/mL). Then, the mixture was reacted under stirring at 55° C. for 24 hours. After the completion of the reaction, the reaction mixture was dried in a boxy dryer at 70° C. for 24 hours. Thus 196 g of enzyme-treated beet pulp (L-arabinose content: 14.5%, moisture content: 9%) was obtained.

Example 6

Enzyme-Treated Beet Pulp

To 200 g of beet pulp (manufactured by Toshoku Ltd., moisture content: 11%) was added 400 mL of an enzyme solution containing 4 mL of Sumizyme PX (pectinase manufactured by Shin Nihon Kagaku Kogyo K.K., pectinase titer: 6000 U/mL, arabinase titer 100 U/mL) dissolved therein. Then, the mixture was reacted under stirring at 55° C. for 24 hours. After the completion of the reaction, the reaction mixture was dried in a boxy dryer at 70° C. for 24 hours. Thus 196 g of enzyme-treated beet pulp (L-arabinose content: 15.2%, moisture content: 9%) was obtained.

Example 7

Enzyme-Treated Beet Pulp

To 200 g of beet pulp (manufactured by Toshoku Ltd., moisture content: 11%) was added 400 mL of an enzyme solution containing 4 mL of Sumizyme ARS (arabinase manufactured by Shin Nihon Kagaku Kogyo K.K., titer: 400 U/mL) and 4 mL of Pectinase PL "AMANO" (manufactured by Amano Seiyaku K.K., titer: 1,500 U/mL) dissolved therein. Then, the mixture was reacted under stirring at 55° C. for 24 hours. After the completion of the reaction, the reaction mixture was dried in a boxy dryer at 70° C. for 24 hours. Thus 195 g of enzyme-treated beet pulp (L-arabinose content: 14.5%, moisture content: 9%) was obtained.

Example 8

Enzyme-Treated Orange Fiber

To 200 g of orange fiber (manufactured by Nutrinova Japan, moisture content: 2%) were added 800 mL of water and 4 mL of Sumizyme ARS (arabinase manufactured by Shin Nihon Kagaku Kogyo K.K., titer: 400 U/mL). Then, the mixture was reacted under stirring at 55° C. for 24 hours. Then, the reaction mixture was dried in a boxy dryer at 70° C. for 24 hours. Thus 210 g of enzyme-treated orange fiber (L-arabinose content: 9.3%, moisture content: 8%) was obtained.

Example 9

Enzyme-Treated Orange Fiber

To 200 g of orange fiber (manufactured by Nutrinova Japan, moisture content: 2%) were added 400 mL of water and 8 mL of Sumizyme PX (pectinase manufactured by Shin Nihon Kagaku Kogyo K.K., pectinase titer: 6000 U/mL, arabinase titer 100 U/mL). After mixing, the mixture was reacted under stirring at 55° C. for 24 hours. Then, the reaction mixture was vacuum-dried (40° C, 72 hours). Thus 190 g of enzyme-treated orange fiber (L-arabinose content: 9%, dietary fiber content: about 50%, moisture content: about 10%) was obtained.

Example 10

Enzyme-Treated Apple Fiber

To 200 g of apple fiber (manufactured by Nutrinova Japan, moisture content: 2%) were added 200 mL of water and 4 mL of Sumizyme ARS (arabinase manufactured by Shin Nihon Kagaku Kogyo K.K., titer: 400 U/mL). After mixing, the mixture was reacted under stirring at 55° C. for 24 hours. Then, the reaction mixture was vacuum-dried (40° C., 48 hours). Thus 195 g of enzyme-treated apple fiber (L-arabinose content: 7%, dietary fiber content: about 50%, moisture content: about 10%) was obtained.

Example 11

Enzyme-Treated Rice Bran

To 200 g of rice bran (manufactured by Tsuno Co.) were added 400 mL of water and 12 mL of Sumizyme PX (pectinase manufactured by Shin Nihon Kagaku Kogyo K.K., pectinase titer: 6000 U/mL, arabinase titer 100 U/mL). After mixing, the mixture was reacted under stirring at 55° C. for 24 hours. Then, the reaction mixture was vacuum-dried (40° C., 24 hours). Thus 190 g of enzyme-treated rice bran (L-arabinose content: 2%, dietary fiber content: about 20%, moisture content: about 6%) was obtained.

Example 12

Enzyme-Treated Peanut Hull

To 200 g of ground peanut hull (prepared from marketed peanuts) were added 400 mL of water and 12 mL of Sumizyme PX (pectinase manufactured by Shin Nihon Kagaku Kogyo K.K., pectinase titer: 6000 U/mL, arabinase titer 100 U/mL). After mixing, the mixture was reacted under stirring at 55° C. for 24 hours. Then, the reaction mixture was vacuum-dried (40° C., 24 hours). Thus 180 g of enzyme-treated peanut hull (L-arabinose content: 2%, dietary fiber content: about 30%, moisture content: about 5%) was obtained.

Example 13

Enzyme-Treated Soybean Cake

To 200 g of okara (residue obtained in producing tofu) (marketed product, moisture content: about 60%) were added 100 mL of water and 3 mL of Sumizyme ARS (arabinase manufactured by Shin Nihon Kagaku Kogyo K.K., titer: 400 U/mL). After mixing, the mixture was reacted under stirring at 55° C. for 24 hours. Then, the reaction mixture was vacuum-dried (40° C., 48 hours). Thus 90 g of enzyme-treated soybean cake (L-arabinose content: 3%, dietary fiber content: about 40%, moisture content: about 10%) was obtained.

Next, processes for producing diet foods and diabetic foods containing L-arabinose and dietary fiber with the use of enzyme-treated products will be illustrated.

Example 14

Cookie Containing Enzyme-Treated Orange Fiber

A dough was prepared by blending 200 g of wheat flour, 100 g of the enzyme-treated orange fiber prepared in Example 9, the yolk of an egg, 100 g of butter, 80 g of powdery sugar and an appropriate amount of sodium chloride (total weight: about 500 g, content of the enzyme-treated orange fiber: about 20% based on the total weight), molded and then baked in an oven at 180° C. for about 10 minutes to give cookies containing the enzyme-treated orange fiber. These enzyme-treated orange fiber-containing cookies contained 2% of L-arabinose and about 10% of dietary fiber.

Example 15

White Bread Containing Enzyme-Treated Soybean Cake

A dough was prepared by blending 400 g of wheat flour, 100 g of the enzyme-treated soybean cake prepared in Example 13, 30 g of butter, one large spoonful of sugar, one small spoonful of sodium chloride, two small spoonfuls of dry yeast and 180 cc of warm water (total weight excluding water: about 550 g, content of the enzyme-treated soybean cake: about 18% based on the total weight), put into a white bread mold and then baked in an oven at 200° C. for about 10 minutes to give white bread containing the enzyme-treated soybean cake. This enzyme-treated soybean cake-containing white bread contained 0.5% of L-arabinose and about 8% of dietary fiber.

Example 16

Cake Containing Enzyme-Treated Apple Fiber

A dough was prepared by blending 90 g of wheat flour, 100 g of the ground enzyme-treated apple fiber (prepared in Example 10), 30 g of butter, 90 g of sugar and 3 eggs (total weight: about 400 g, content of the enzyme-treated apple fiber: about 25% based on the total weight), poured into a mold and then baked in an oven at 180° C. for about 25 minutes to give a cake containing the enzyme-treated apple fiber. This enzyme-treated apple fiber-containing cake contained 2% of L-arabinose and about 12% of dietary fiber.

Example 17

Ice Cream Containing Enzyme-Treated Rice Bran

A mixture of 400 cc of cow's milk, the yolk of 4 eggs, 100 g of sugar, 200 cc of fresh cream and 200 g of the enzyme-treated rice bran (prepared in Example 11) (total weight: about 1000 g, content of the enzyme-treated rice bran: about 20% based on the total weight) was solidified under agitation in an apparatus for producing ice cream to give ice cream containing the enzyme-treated rice bran. This enzyme-treated rice bran-containing ice cream contained 0.5% of L-arabinose and about 5% of dietary fiber.

Example 18

Hand-Made Udon Noodles Containing Enzyme-Treated Peanut Hull

A dough was prepared by blending 800 g of wheat flour, 200 g of the ground enzyme-treated peanut hull (prepared in Example 12), 30 g of sodium chloride and 390 g of water (total weight: about 1500 g, content of the enzyme-treated peanut hull: about 13% based on the total weight), spread out and molded to give hand-made udon noodles containing the enzyme-treated peanut hull. This enzyme-treated peanut hull-containing hand-made udon noodles contained 0.3% of L-arabinose and about 4% of dietary fiber.

Example 19

Tablets Containing Enzyme-Treated Orange Fiber

A mixture comprising 15 g of sugar, 7 g of L-ascorbic acid, a filler, perfume and a colorant, each in an appropriate amount, and 75 g of the enzyme-treated orange fiber (prepared in Example 9) (content of the enzyme-treated orange fiber: about 75% based on the total weight) was directly tabletted by the powder-compression method to give tablets each containing 1.5 g of the enzyme-treated orange fiber. These enzyme-treated orange fiber-containing tablets contained 7% of L-arabinose and about 36% of dietary fiber.

Next, the effects of the diet foods and diabetic foods thus prepared on blood glucose level and bowel movement will be illustrated.

Example 20

Test of Cookies Containing Enzyme-Treated Orange Fiber: Blood Glucose Level

The enzyme-treated orange fiber-containing cookies (L-arabinose content: 2%) prepared in Example 14 were given at 10:00 a.m. to 10 normal adults (6 males and 4 males) without having the previous evening meal and breakfast. Before the intake and 30, 60 and 120 minutes thereafter, changes in the peripheral blood glucose level were monitored by using an apparatus for measuring blood glucose level and blood glucose level measuring paper (Tide and Tidex, both manufactured by Bayer Medical-Sankyo). For comparison, cookies prepared in the conventional manner (Comparative Example 2), cookies containing 2% of L-arabinose alone (Comparative Example 3) and cookies containing untreated orange fiber alone (Comparative Example 4) were also tested in the same manner. The data were expressed in changes (the average of 10 subjects) after the intake by referring the blood glucose level before the intake as to 0.

TABLE 2

| Cookie | Ex. 14 | Comp. Ex. 2 | Comp. Ex. 3 | Comp. Ex. 4 |
|---|---|---|---|---|
| Before intake | 0 | 0 | 0 | 0 |
| 30 min after intake | +30 | +68 | +55 | +63 |
| 60 min after intake | +18 | +52 | +42 | +49 |
| 120 min after intake | −1 | +16 | +14 | +14 |

Table 2 shows changes in the blood glucose level caused by taking various cookies. The intake of the cookies of Comparative Example 2 caused an obvious increase in the blood glucose level compared with the value before the intake. In comparison, the increase in the blood glucose level was suppressed to about 80% in the case of the cookies of Comparative Example 3. The cookies of Comparative Example 4 suppressed the increase in the blood glucose level only slightly. However, the intake of the cookies of Example 14 suppressed the increase in the blood glucose level to about 40% in the case of taking the cookies of Comparative Example 2. These results indicate that the enzyme-treated orange fiber-containing cookies have a stronger effect of inhibiting an increase in blood glucose level than L-arabinose. Namely, the effect of L-arabinose of inhibiting an increase in blood glucose level is enhanced by the presence of the dietary fiber.

Example 21

Test of Enzyme-Treated Rice Bran-Containing Ice Cream: Bowel Movement

The enzyme-treated rice bran-containing ice cream (L-arabinose content: 0.5%, dietary fiber content: about 5%) prepared in Example 17 was given to 10 adults (3 males and 7 females) with a tendency to constipation. Each monitor took a cup of the ice cream (100 g) at 9:00 p.m. everyday for 1 week and the effect of improving the bowel movement was sensorily evaluated. The evaluation was made in 5 grades and a higher score meant a better result. The results are expressed in the average of 10 monitors.

TABLE 3

| Evaluation item | Score |
|---|---|
| Bowel movement frequency (Good = Increased) | 3.7 |
| Amount of feces (Good = Increased) | 4.3 |
| Regularity in bowel movement (Good = More regular) | 4.7 |
| Hardness of feces (Good = Softened) | 4.0 |

Table 3 shows the results of the sensory test of Example 21. The intake of the enzyme-treated rice bran-containing ice cream showed an improving effect in each evaluation item, which indicates that the enzyme-treated rice bran-containing ice cream has a favorable effect of ameliorating intestinal disorder.

Next, processes for producing L-arabinose-containing fruit or vegetable juices will be illustrated.

Example 22

Apple Juice Containing L-arabinose-Containing Fraction

Three apples with peel were ground in a juicer and pressed by using filter cloth to give 590 mL of apple juice and 118 g of press cake (moisture content: 60%) To this press apple juice cake, 1.18 g of Sumizyme ARS (arabinase manufactured by Shin Nihon Kagaku Kogyo K.K., titer: 400 U/mL) was added and the mixture was reacted at 55° C. for 24 hours. This enzyme-treated product contained 2.2% (w/w) of o10 L-arabinose. To 60 g of this L-arabinose-containing apple juice cake was added the apple juice obtained by pressing to give a total volume of 0.5 L. Thus, an L-arabinose-containing apple juice (L-arabinose concentration: 2.6 g/L) was obtained.

Example 23

Orange Juice Containing L-arabinose-Containing Fraction

Five oranges were squeezed with hands to give 320 mL of orange juice and 430 g of press cake (moisture content: 60%). Then, 4.3 g of Sumizyme PX (pectinase manufactured by Shin Nihon Kagaku Kogyo K.K., pectinase titer: 6000 U/mL, arabinase titer 100 U/mL) was added and thereto the mixture was reacted at 55° C. for 24 hours. The reaction mixture was pressed to give 150 mL of a solution containing L-arabinose. By analyzing saccharides contained in this solution, it was found out that the L-arabinose concentration of this solution was 25 g/L. To 60 mL of this L-arabinose-containing solution originating in the press orange juice cake added orange juice to give a total volume of 0.5 L. Thus, an L-arabinose-containing orange juice (L-arabinose concentration: 3.0 g/L) was obtained.

Example 24

Pear Juice Containing L-arabinose-Containing Fraction

Three pears with peel were ground in a juicer and pressed by using filter cloth to give 390 mL of pear juice and 43 g of press cake (moisture content: 68%). To 43 g of this press pear juice cake, 0.43 mL of Sumizyme ARS (arabinase manufactured by Shin Nihon Kagaku Kogyo K.K., titer: 400 U/mL) was added and the mixture was reacted at 55° C. for 24 hours. The reaction mixture was pressed to give 15 mL of a solution containing 32 g/L of L-arabinose. 15 mL of this L-arabinose-containing solution originating in the press pear juice cake was mixed with 135 mL of pear juice to give 150 mL of an L-arabinose-containing pear juice (L-arabinose concentration: 3.2 g/L).

Example 25

Carrot Juice Containing L-arabinose-Containing Fraction

To 500 g of press carrot juice cake (moisture content: 60%) was added 5 mL of Sumizyme ARS (arabinase manufactured by Shin Nihon Kagaku Kogyo K.K., titer: 400 U/mL) and the obtained mixture was reacted at 55° C. for 24 hours. Then, the reaction mixture was pressed to give 110 mL of a solution containing 11 g/L of L-arabinose. 100 mL of this L-arabinose-containing solution originating in the press carrot juice cake was mixed with 300 mL of carrot juice to give 400 mL of an L-arabinose-containing carrot juice (L-arabinose concentration: 2.8 g/L).

Next, the effects of the L-arabinose-containing fruit or vegetable juices on blood glucose level will be illustrated.

Example 26

Test 1 for Confirming Effect of Inhibiting Increase in Blood Glucose Level 100 mL of the L-arabinose-containing apple juice obtained in Example 22 was given together with 10 g of sucrose to normal adults and changes in the blood glucose level after intake were monitored. For comparison, a 100% apple juice containing no L-arabinose-containing apple juice cake (Comparative Example 5) and an apple juice containing 2.6 g/L of an L-arabinose reagent (manufactured by Ishizu Seiyaku K.K.) (Comparative Example 6) were tested in the same manner and the data of these groups were compared. FIG. 1 shows the results of Example 26.

As FIG. 1 shows, the increase in the blood glucose level after the intake was inhibited in the group with the intake of the apple juice containing the L-arabinose-containing fraction (Example 22), compared with the L-arabinose-free group of Comparative Example 5. It was also clarified that a higher effect was achieved in the group with the intake of the apple juice containing the L-arabinose-containing fraction than in Comparative Example 2 with the addition of the L-arabinose reagent.

Example 27

Figure 2:
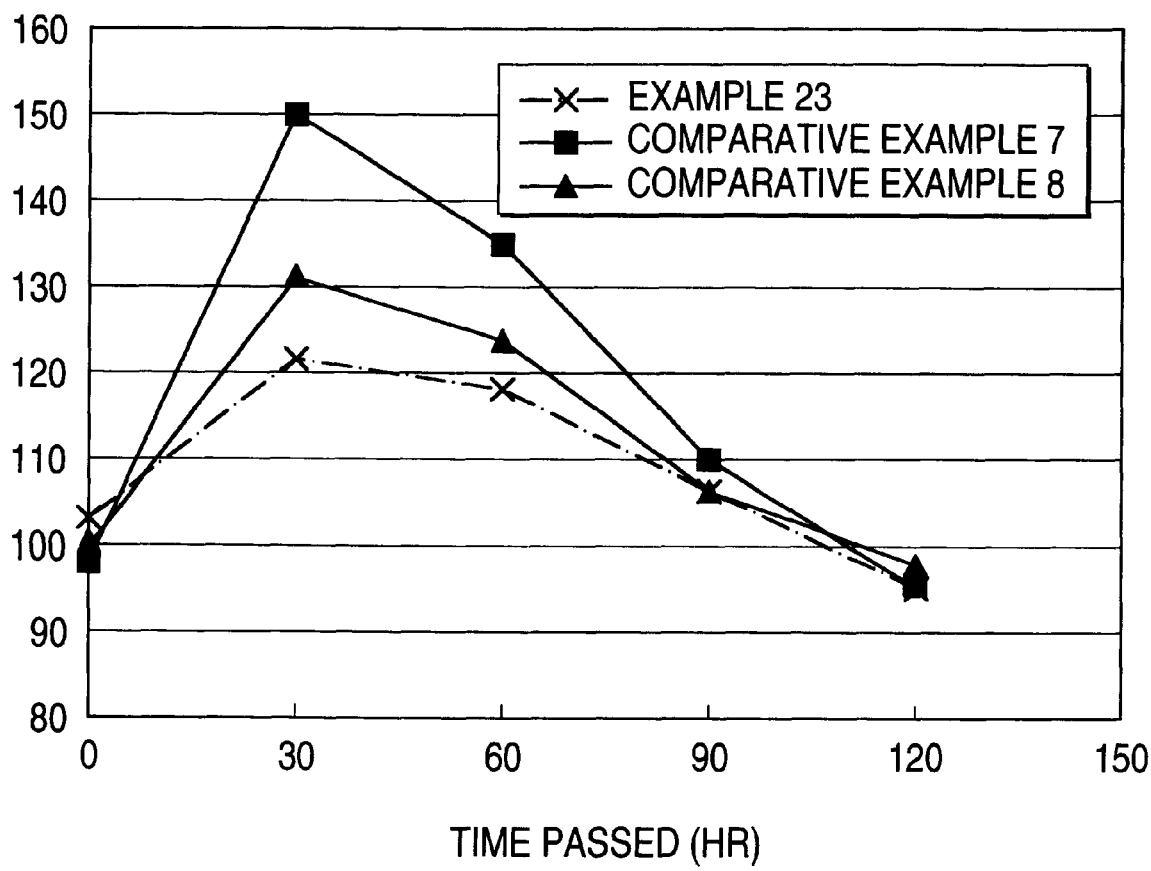
FIG. 2 is a graph which shows the data concerning the effect of inhibiting an increase in blood glucose level in Example 27.

Test 2 for Confirming Effect of Inhibiting Increase in Blood Glucose Level 100 mL of the L-arabinose-containing orange juice obtained in Example 23 was given together with 10 g of sucrose to normal adults and changes in the blood glucose level after intake were monitored. For comparison, a 100% orange juice containing no L-arabinose-containing solution originating in the orange juice cake (Comparative Example 7) and an orange juice containing 3.0 g/L of an L-arabinose reagent (manufactured by Ishizu Seiyaku K.K.) (Comparative Example 8) were tested in the same manner and the data of these groups were compared. FIG. 2 shows the results of Example 27.

As FIG. 2 shows, the increase in the blood glucose level after the intake was inhibited in the group with the intake of the orange juice containing the L-arabinose-containing fraction (Example 23), compared with the L-arabinose-free group of Comparative Example 7. It was also clarified that a higher effect was achieved in the group with the intake of the orange juice containing the L-arabinose-containing fraction than in Comparative Example 8 with the addition of the L-arabinose reagent.

INDUSTRIAL APPLICABILITY

According to the process of the invention, L-arabinose and enzyme-treated products containing L-arabinose can be easily and economically prepared from natural substances containing arabinan, arabinoxylan or arabinogalactan, which are less expensive materials, without resort to any troublesome procedure (for example, preliminarily taking out arabinan, arabinoxylan or arabinogalactan). The obtained products are applicable to diet foods and diabetic foods having effects of inhibiting an increase in blood glucose level and ameliorating bowel movement due to L-arabinose and dietary fiber. Moreover, L-arabinose-containing fruit or vegetable juices having functions of, inhibiting an increase in blood glucose level, etc. imparted thereto can be provided by adding L-arabinose-containing press juice cake or a solution obtained therefrom by solid/liquid separation. These techniques make it possible to enlarge the use of agricultural crops which have been dumped as wastes, thereby largely contributing to the enhancement of the consumption thereof. In addition, fear of undesirable effects on the environment caused by dumping can be relieved thereby.

What is claimed is:

1. A process for producing L-arabinose by treating a natural material containing arabinan, arabinoxylan or arabinogalactan with an enzyme having an activity of acting on the natural material containing arabinan, arabinoxylan or arabinogalactan and thus releasing L-arabinose to give L-arabinose, wherein said natural material is directly treated with said enzyme without separating or extracting arabinan, arabinoxylan or arabinogalactan from said natural material to give an enzyme-treated product having released L-arabinose at a ratio of at least 2.1 g per 100 g of the starting material, as solid matter, and then L-arabinose is obtained from said enzyme-treated product.

2. The process for producing L-arabinose as claimed in claim 1, wherein said enzyme having an activity of acting on a natural material containing arabinan, arabinoxylan or arabinogalactan and thus releasing L-arabinose is an enzyme which degrades arabinan, arabinoxylan or arabinogalactan.

3. The process for producing L-arabinose as claimed in claim 1, wherein said natural material containing arabinan, arabinoxylan or arabinogalactan is one or more members selected from among orange, mandarin orange, apple, beet, peanut, corn, rice, wheat, soybean, orange fiber, mandarin orange juice cake, apple fiber, apple juice cake, beet fiber, beet pulp, peanut cake, rice bran, corn cake and soybean cake.

4. An enzyme-treated product containing L-arabinose which is prepared by treating a natural material containing arabinan, arabinoxylan or arabinogalactan directly with an enzyme having an activity of acting on a natural material containing arabinan, arabinoxylan or arabinogalactan and thus releasing L-arabinose to thereby release L-arabinose at a ratio of at least 2.1 g per 100 g of the starting material, as solid matter.

5. A process for producing an enzyme-treated product containing L-arabinose comprising releasing L-arabinose by treating a natural material containing arabinan, arabinoxylan or arabinogalactan directly with an enzyme having an activity of acting on the natural material containing arabinan, arabinoxylan or arabinogalactan and thus releasing L-arabinose to thereby release L-arabinose at a ratio of at least 2.1 g per 100 g of the starting material, as solid matter, to give the enzyme-treated product containing L-arabinose as claimed in claim 4.

6. A process for producing L-arabinose or an enzyme-treated product containing L-arabinose comprising treating a natural material containing arabinan, arabinoxylan or arabinogalactan directly with an enzyme which degrades L-arabinose together with pectinase to thereby release L-arabinose at a ratio of at least 2.1 g per 100 g of the starting material, as solid matter, without separating or extracting arabinan, arabinoxylan or arabinogalactan from said natural material.

7. A diet food characterized by comprising L-arabinose and dietary fiber.

8. The diet food as claimed in claim 7, wherein said L-arabinose and dietary fiber are obtained by treating a dietary fiber material originating in a natural material containing arabinan, arabinoxylan or arabinogalactan with an enzyme.

9. A process for producing a diet food comprising treating a dietary fiber material originating in a natural material containing arabinan, arabinoxylan or arabinogalactan directly with an enzyme which degrades arabinan, arabinoxylan or arabinogalactan to give an enzyme-treated product containing L-arabinose released at a ratio of at least 2.1 g per 100 g of the starting material, as solid matter, and dietary fiber, and adding the thus obtained enzyme-treated product to a food.

10. A diabetic food characterized by comprising L-arabinose and dietary fiber.

11. The diabetic food as claimed in claim 10, wherein said L-arabinose and dietary fiber are obtained by treating a dietary fiber material originating in a natural material containing arabinan, arabinoxylan or arabinogalactan with an enzyme.

12. A process for producing a diabetic food comprising treating a dietary fiber material originating in a natural material containing arabinan, arabinoxylan or arabinogalactan directly with an enzyme which degrades arabinan, arabinoxylan or arabinogalactan to give an enzyme-treated product containing L-arabinose released at a ratio of at least 2.1 g per 100 g of the starting material, as solid matter, and dietary fiber, and adding the thus obtained enzyme-treated product to a food.

13. An L-arabinose-containing fruit or vegetable juice containing a fraction containing L-arabinose released at a ratio of at least 2.1 g per 100 g of the starting material, as solid matter, obtained by treating a fruit or vegetable press cake containing arabinan, arabinoxylan or arabinogalactan directly with an enzyme.

14. A process for producing an arabinose-containing fruit or vegetable juice comprising treating a fruit or a vegetable containing arabinan, arabinoxylan or arabinogalactan to obtain a juice and a press juice cake, treating the press juice cake directly with an enzyme to release L-arabinose at a ratio of at least 2.1 g per 100 g of the starting material, as solid matter, and then adding the fraction containing the released L-arabinose to the juice.

15. A method of inhibiting an increase in blood glucose level which comprises administering an effective amount of L-arabinose obtained by a process as claimed in claim 1 or an enzyme-treated product containing L-arabinose obtained by a process for producing an enzyme-treated product containing L-arabinose characterized by comprising treating a natural material containing arabinan, arabinoxylan or arabinogalactan directly with an enzyme having an activity of acting on the natural material containing arabinan, arabinoxylan or arabinogalactan and thus releasing L-arabinose to thereby release L-arabinose at a ratio of at least 2.1 g per 100 g of the starting material, as solid matter, to give the enzyme-treated product; or obtained by a process for producing an enzyme-treated product containing L-arabinose comprising treating a natural material containing arabinan, arabinoxylan or arabinogalactan directly with an enzyme which degrades arabinan, arabinoxylan or arabinogalactan together with pectinase to thereby without separating or extracting arabinan, arabinoxylan or arabinogalactan from said natural material; and then administering said L-arabinose to a subject.

16. A method of inhibiting an increase in blood glucose level which comprises administering an effective amount of L-arabinose obtained by a process as claimed in claim 8 or an enzyme-treated product containing L-arabinose obtained by a process for producing an enzyme-treated product containing L-arabinose characterized by comprising treating a natural material containing arabinan, arabinoxylan or arabinogalactan directly with an enzyme having an activity of acting on the natural material containing arabinan, arabinoxylan or arabinogalactan and thus releasing L-arabinose to thereby release L-arabinose at a ratio of at least 2.1 g per 100 g of the starting material, as solid matter, to give the enzyme-treated product; or obtained by a process for producing an enzyme-treated product containing L-arabinose comprising treating a natural material containing arabinan, arabinoxylan or arabinogalactan directly with an enzyme which degrades arabinan, arabinoxylan or arabinogalactan together with pectinase to thereby release L-arabinose at a ratio of at least 2.1 g per 100 g of the starting material, as solid matter, without separating or extracting arabinan, arabinoxylan or arabinogalactan from said natural material; and then administering said L-arabinose to a subject.

17. The process for producing L-arabinose as claimed in claim 1, wherein said natural material is directly treated by being suspended in an aqueous medium and then said enzyme is added to said natural material suspended in said aqueous medium.

18. The enzyme-treated product containing L-arabinose as claimed in claim 4, wherein said treating directly of said natural material with an enzyme comprises suspending said natural material in an aqueous medium and then said enzyme is added to said natural material suspended in said aqueous medium.

19. A process for producing an enzyme-treated product containing L-arabinose as claimed in claim 5, wherein said releasing L-arabinose by treating said natural material directly with an enzyme comprises suspending said natural material in an aqueous medium and then adding said enzyme to said natural material suspended in said aqueous medium.

20. A process for producing L-arabinose or an enzyme-treated product containing L-arabinose as claimed in claim 6, wherein said treating of said natural material directly with an enzyme comprises suspending said natural material in an aqueous medium and then adding said enzyme to said natural material in said aqueous medium.

21. A process for producing a diet food as claimed in claim 9, wherein said treating of said dietary fiber material directly with said enzyme comprises suspending said dietary fiber material in an aqueous medium and then adding said enzyme to said dietary fiber material suspended in said aqueous medium.

22. A process for producing a diabetic food as claimed in claim 12, wherein said treating of said dietary fiber material directly with an enzyme comprises suspending said dietary fiber material in an aqueous medium and then adding said enzyme to said dietary fiber material suspended in said aqueous medium.

23. The L-arabinose-containing fruit or vegetable juice as claimed in claim 13, wherein said treating of said fruit or vegetable press cake directly with an enzyme comprises suspending said fruit or vegetable press cake in an aqueous medium and then adding said enzyme to said fruit or vegetable press cake suspended in said aqueous medium.

24. A process for producing an arabinose-containing fruit or vegetable juice as claimed in claim 14, wherein said treating of said press juice cake directly with an enzyme comprises suspending said press juice cake in an aqueous medium and then adding said enzyme to said press fruit cake suspended in said aqueous medium.

25. A method of inhibiting an increase in blood glucose level as claimed in claim 18, wherein said treating said natural material directly with said enzyme or treating said natural material directly with said enzyme together with pectinase comprises suspending said natural material in an aqueous medium and then adding said enzyme or said enzyme together with pectinase to said natural material suspended in said aqueous medium.

26. A method of inhibiting an increase in blood glucose level as claimed in claim 16, wherein said treating a natural material directly with said enzyme or treating said natural material directly with said enzyme together with pectinase comprises suspending said natural material in an aqueous medium and then adding said enzyme or said enzyme together with pectinase to said natural material suspended in said aqueous medium.

* * * * *